US010568875B2

(12) United States Patent
Puri et al.

(10) Patent No.: US 10,568,875 B2
(45) Date of Patent: *Feb. 25, 2020

(54) ATROPINE PHARMACEUTICAL COMPOSITIONS

(71) Applicant: Nevakar Inc., Bridgewater, NJ (US)

(72) Inventors: Navneet Puri, Lebanon, NJ (US); Prem Sagar Akasapu, Edison, NJ (US); Irfan A. Mohammed, Cherry Hill, NJ (US); Kumaresh Soppimath, Skillman, NJ (US); Iouri V. Ilitchev, Hillsborough, NJ (US)

(73) Assignee: Nevakar Inc., Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/280,384

(22) Filed: Feb. 20, 2019

(65) Prior Publication Data

US 2019/0209545 A1 Jul. 11, 2019

Related U.S. Application Data

(62) Division of application No. 15/976,279, filed on May 10, 2018, now Pat. No. 10,251,875.

(60) Provisional application No. 62/505,027, filed on May 11, 2017.

(51) Int. Cl.

| A61K 31/46 | (2006.01) |
| A61K 9/08 | (2006.01) |
| A61K 9/00 | (2006.01) |
| A61K 47/18 | (2017.01) |
| A61K 47/38 | (2006.01) |
| A61K 47/02 | (2006.01) |

(52) U.S. Cl.
CPC ............ *A61K 31/46* (2013.01); *A61K 9/0048* (2013.01); *A61K 9/08* (2013.01); *A61K 47/02* (2013.01); *A61K 47/183* (2013.01); *A61K 47/38* (2013.01)

(58) Field of Classification Search
CPC ........ A61K 31/46; A61K 9/08; A61K 9/0048; A61K 47/02; A61K 47/183; A61K 47/38
USPC ........................................................ 514/304
See application file for complete search history.

(56) References Cited

U.S. PATENT DOCUMENTS

| 6,164,282 A | 12/2000 | Gwon et al. |
| 7,491,383 B2 | 2/2009 | Woodward et al. |
| 8,758,816 B2 | 6/2014 | Fuge et al. |
| 9,421,199 B2 | 8/2016 | Ostrow et al. |
| 10,251,875 B2 * | 4/2019 | Puri ...................... A61K 31/46 |
| 2007/0254914 A1 | 11/2007 | Wu et al. |
| 2016/0009705 A1 | 1/2016 | Ostrow et al. |
| 2016/0067238 A1 | 3/2016 | Wu et al. |
| 2016/0338947 A1 | 11/2016 | Leahy et al. |
| 2018/0042911 A1 | 2/2018 | Ostrow et al. |
| 2019/0091213 A1 | 3/2019 | Ostrow et al. |
| 2019/0175579 A1 * | 6/2019 | Puri ...................... A61K 31/46 |
| 2019/0175580 A1 * | 6/2019 | Puri ...................... A61K 31/46 |
| 2019/0183876 A1 * | 6/2019 | Puri ...................... A61K 31/46 |
| 2019/0192499 A1 | 6/2019 | Puri et al. |

FOREIGN PATENT DOCUMENTS

| JP | 1-203320 | 2/1988 |
| JP | 2007308398 A | 11/2007 |
| WO | 2012161655 A1 | 11/2012 |
| WO | 2015200361 A1 | 12/2015 |
| WO | 2016172712 A2 | 10/2016 |
| WO | WO-2016172712 A2 * | 10/2016 ............... A61K 9/08 |
| WO | 2016205069 A1 | 12/2016 |
| WO | 2017204262 A1 | 11/2017 |

OTHER PUBLICATIONS

Lund, Walter, et al. "The Kinetics of Atropine and Apoatropine in Aqueous Solutions." Acta Chemica Scandinavica, vol. 22, 1968, pp. 3085-3097.
Parry, Nicola, et al. "How to Use Low-Dose Atropine to Slow Myopic Progression in Kids." Eyenet Magazine, Dec. 2016, pp. 29-31.
Schier, Joshua G., et al. "Preparing for Chemical Terrorism: Stability of Injectable Atropine Sulfate." Academic Emergency Medicine, vol. 11, No. 4, 2004, pp. 329-334.
Cristina et al., "Preservatives From the Eye Drops and the Ocular Surface", Romanian Journal of Ophthalmology, Mar. 2015, vol. 59, No. 1, pp. 2-5.

* cited by examiner

*Primary Examiner* — Yong L Chu
(74) *Attorney, Agent, or Firm* — Umberg Zipser LLP

(57) ABSTRACT

The inventive subject matter is directed to compositions and methods for sterile and storage stable low-dose atropine formulations with improved stability. Most preferably, the compositions presented herein are substantially preservative free and exhibit less than 0.35% tropic acid from degradation of atropine. Advantageously, contemplated formulations are also substantially free of preservatives.

20 Claims, 1 Drawing Sheet

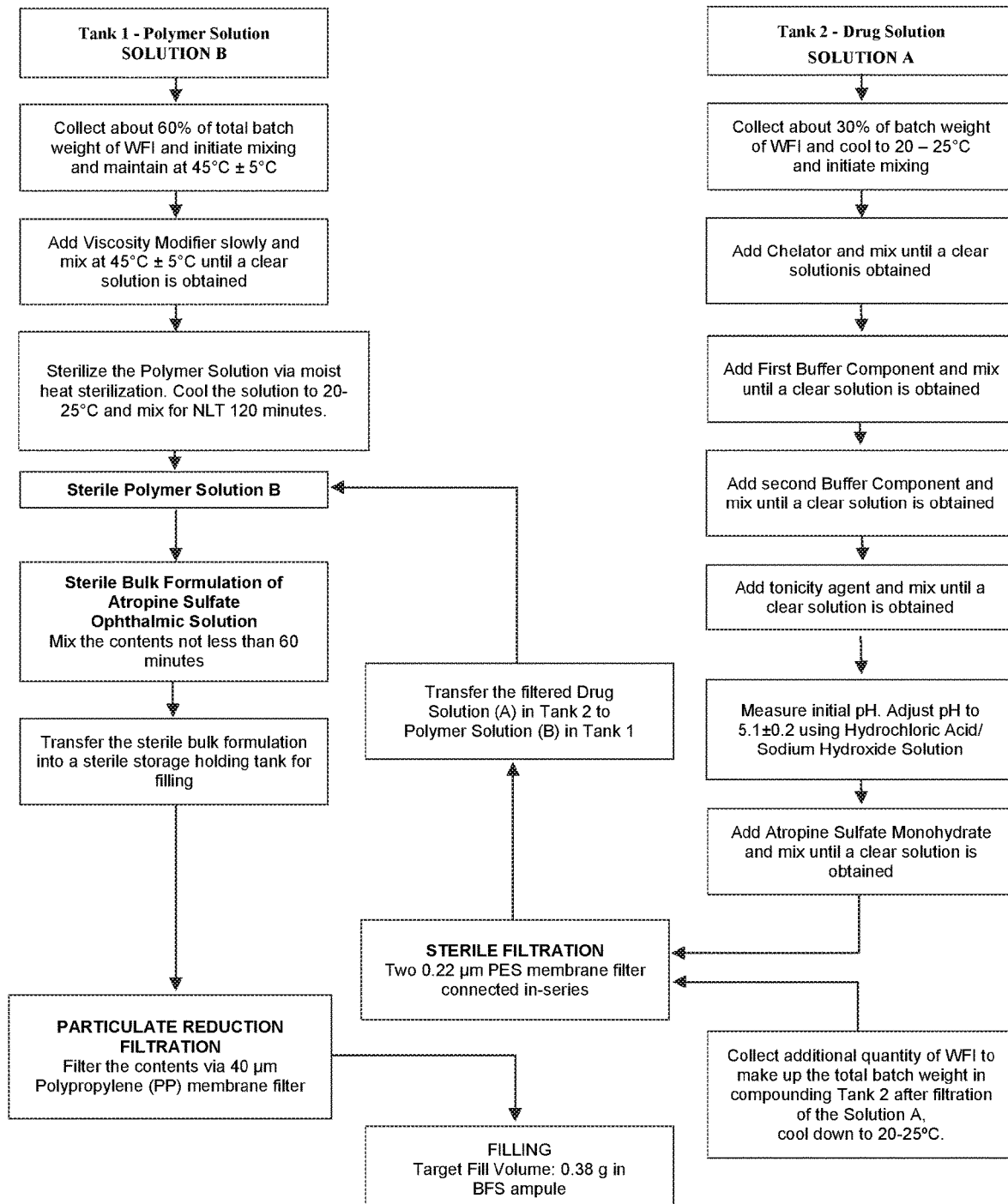

ATROPINE PHARMACEUTICAL COMPOSITIONS

This application is a continuation application of U.S. application with the Ser. No. 15/976,279, which was filed May 10, 2018, now U.S. Pat. No. 10,251,875, and which claims priority to US provisional application with the Ser. No. 62/505,027, which was filed May 11, 2017.

FIELD OF THE INVENTION

The field of the invention is pharmaceutical compositions comprising atropine sulfate, especially as it relates to various storage stable, ready-to-use, preservative free compositions, and method of manufacturing such compositions.

BACKGROUND

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Atropine is the tropine ester of tropic acid and is generally available as the sulfate salt. Nonenzymatic spontaneous hydrolysis of aqueous atropine yields tropine and tropic acid that are nontoxic but do not have biological activity in ophthalmic use. Stability has been tested, for example, for certain injectable formulations and degradation was observed over time for in-date and out-of-date formulations (*Acad Emerg Med April* 2004, Vol. 11, No. 4:329-334). Notably, atropine loss was significant in most cases, but less than 25% of the starting concentration. However, these formulations included atropine at high concentrations between 0.4 mg/ml and 2 mg/ml and had a very low pH (typically equal or less than pH4), which is in most cases unsuitable for ophthalmic use.

In ophthalmic use, atropine is marketed as Atropine Care (Akorn) formulated as a 1% drug solution for treatment of amblyopia and further contains 0.01% w/w of the preservative benzalkonium chloride. In another indication, atropine has also been used in several pediatric studies to slow down the progression of myopia. More specifically, children who received topically administered atropine drops had a slower disease progression than a control group in the same study. Advantageously, children receiving eye drops containing low atropine concentrations (e.g., in the range of 0.01-0.05%% w/v (0.01% w/w)) had significantly less photophobia and other side effects (see e.g., *Ophthalmology*, 2015: 1-9). Indeed, the use of low-dose (i.e., 0.01%) atropine has become a preferred treatment of choice in slowing the progression of myopia. Unfortunately, the toxic effects of benzalkonium chloride have been demonstrated in the lab and in the clinic, and include tear film instability, loss of goblet cells, conjunctival squamous metaplasia and apoptosis, disruption of the corneal epithelium barrier, and damage to deeper ocular tissues (see e.g., *Prog Retin Eye Res.* 2010 Jul. 29 (4):312-34).

In still further known compositions and methods, atropine formulations are described in WO 2017/204262 that include various buffer ingredients and water soluble polymers in which most formulations had a pH of about 4.3, 4.5, or 5.0 at an atropine concentration of 0.01% w/w. While such formulations were shown to reduce progression of myopia without exacerbating mydriatic action of atropine, stability of atropine as measured by an increase in tropic acid was less than desirable within as little as four weeks.

As normal tears have a pH of about 7.4, an ophthalmic solution should have the same pH as the lacrimal fluid. However, this is a challenge for an ophthalmic solutions containing atropine sulfate, as atropine sulfate is subjected to a greater degree of hydrolysis in solutions that are closer to neutral and basic pH conditions. Thus, atropine is more stable in ophthalmic solutions with a more acidic pH. For example, Atropine Care with a 1% w/w concentration of atropine is maintained at pH 5.5, but the shelf life is still limited to 15 months. Moreover, the degradation of atropine to tropic acid in aqueous solution is notably accelerated with reduced concentrations of atropine (e.g., U.S. Pat. No. 9,421,199), which still further compounds stability issues, particularly in low-dose atropine formulations.

To reduce hydrolytic degradation, water in low-dose atropine formulations can be at least in part replaced with deuterated (heavy) water as is described in the U.S. Pat. No. 9,421,199 patent. While conceptually attractive to use kinetic isotope effects in stability, various disadvantages nevertheless remain. Among other things, at least some of the formulations of the '199 patent still contained a preservative. Moreover, deuterated water is still known to be subject to H/D exchange, and as such delivers deuterium to a subject receiving such formulations.

Alternatively, atropine may also be delivered at reduced concentrations from a cross-linked non-degradable polymer matrix as is described in US 2016/0338947. Unfortunately, to maintain the polymer away from the cornea, a shaped implant must be worn on the sclera that is typically not well tolerated or may produce discomfort.

Therefore, there is a need for improved storage stable ready-to-use compositions that contain atropine at low concentrations, have a physiologically desirable pH, and preferably do not contain a preservative.

SUMMARY OF THE INVENTION

The inventive subject matter is directed to ready-to-use atropine compositions having improved stability and a physiologically acceptable pH. Most preferably, such compositions are also substantially preservative free.

In one aspect of the inventive subject matter, the inventors contemplate a liquid storage-stable low-dose ophthalmic atropine composition that comprises an aqueous solution comprising a buffer, a tonicity agent, a viscosity modifier, and atropine or a pharmaceutically acceptable salt thereof, wherein the atropine or the pharmaceutically acceptable salt thereof is present in the ophthalmic atropine composition in an amount of equal or less than 0.05 wt %, wherein the buffer has a concentration of equal or less than 75 mM, and wherein the ophthalmic atropine composition has a pH of between 5.0 and 6.0, and wherein the ophthalmic atropine composition is formulated such that after storage over at least two months at 25° C. and 60% relative humidity equal or less than 0.35% tropic acid is formed from degradation of the atropine.

Preferably, atropine or the pharmaceutically acceptable salt thereof is atropine sulfate, and is present in the ophthalmic atropine composition in an amount of equal or less than 0.02 wt %, or in an amount of equal or less than 0.01 wt %, or in an amount of between 0.01% and 0.05 wt %, or in an amount of between 0.001 wt % and 0.01 wt %. Most typically, the buffer has a concentration of equal or less than 60 mM, or equal or less than 50 mM. It is further contemplated that the buffer comprises monobasic and dibasic sodium phosphate. In further embodiments, the composition will further comprise a chelator, typically a bicarboxylic acid, a tricarboxylic acid, or an aminopolycarboxylic acid, and the chelator is present in the ophthalmic atropine composition in an amount of equal or less than 0.01 w %.

Additionally, it is contemplated that the ophthalmic atropine composition has a pH of 5.0 (+/−0.2), or has a pH of 5.5 (+/−0.2), or has a pH of 6.0 (+/−0.2). The tonicity agent is preferably a pharmaceutically acceptable salt that is present in the ophthalmic atropine composition in an amount of between 0.2 wt % and 0.8 wt %. In still further embodiments, the viscosity modifier is a modified cellulose, and preferably a hydroxyethyl cellulose, a hydroxypropyl cellulose, or a hydroxypropyl methylcellulose. Moreover, it is generally preferred that the ophthalmic atropine composition is substantially free of a preservative.

Therefore, the inventors also contemplate a liquid storage-stable low-dose ophthalmic atropine composition that consists essentially of an aqueous solution comprising a buffer, a tonicity agent, a chelator, a viscosity modifier, and atropine or a pharmaceutically acceptable salt thereof. In such compositions it is preferred that the atropine or the pharmaceutically acceptable salt thereof is present in the ophthalmic atropine composition in an amount of equal or less than 0.05 wt %, that the buffer has a concentration of equal or less than 75 mM, and that the ophthalmic atropine composition has a pH of between 5.0 and 6.0. Moreover, such ophthalmic atropine compositions are formulated such that after storage over at least two months at 25° C. and 60% relative humidity equal or less than 0.35% tropic acid is formed from degradation of the atropine.

Most typically, the atropine or the pharmaceutically acceptable salt thereof is atropine sulfate, and the atropine or a pharmaceutically acceptable salt thereof is present in the ophthalmic atropine composition in an amount of equal or less than 0.02 wt %, or in an amount of equal or less than 0.01 wt %, or in an amount of between 0.001 wt % and 0.01 wt %. In some embodiments, the buffer has a concentration of equal or less than 60 mM, or has a concentration of equal or less than 50 mM. it is further contemplated that the buffer comprises monobasic and dibasic sodium phosphate. The chelator is typically a bicarboxylic acid, a tricarboxylic acid, or an aminopolycarboxylic acid. For example, suitable chelators include ethylenediaminetetraacetic acid (EDTA), typically present in the ophthalmic atropine composition in an amount of equal or less than 0.01 wt %.

In other embodiments, the ophthalmic atropine composition has a pH of between 5.0 (+/−0.2) and 5.5 (+/−0.2), or has a pH of between 5.5 (+/−0.2) and 6.0 (+/−0.2), and/or the tonicity agent is a pharmaceutically acceptable salt that is present in the ophthalmic atropine composition in an amount of between 0.2 wt % and 0.8 wt %. Suitable viscosity modifiers include a hydroxyethyl cellulose, a hydroxypropyl cellulose, and a hydroxypropyl methylcellulose. Most typically, the ophthalmic atropine composition is substantially free of a preservative.

For example, contemplated compositions include those in which the atropine or a pharmaceutically acceptable salt thereof is present in the ophthalmic atropine composition in an amount of between 0.001 wt % and 0.01 wt %, wherein the buffer comprises monobasic and dibasic sodium phosphate and has a concentration of equal or less than 50 mM, wherein the viscosity modifier is a hydroxyethyl cellulose, a hydroxypropyl cellulose, or a hydroxypropyl methylcellulose, and wherein the ophthalmic atropine composition is substantially free of a preservative. In other examples, contemplated compositions include those in which the atropine or a pharmaceutically acceptable salt thereof is present in the ophthalmic atropine composition in an amount of between 0.01 wt % and 0.05 wt %, wherein the buffer comprises monobasic and dibasic sodium phosphate and has a concentration of equal or less than 50 mM, wherein the viscosity modifier is a hydroxyethyl cellulose, a hydroxypropyl cellulose, or a hydroxypropyl methylcellulose, and wherein the ophthalmic atropine composition is substantially free of a preservative.

Viewed from a different perspective, the inventors also contemplate a storage-stable preservative-free ophthalmic atropine composition that comprises an aqueous solution comprising low-dose atropine or a pharmaceutically acceptable salt thereof, a low-strength buffer, a pharmaceutically acceptable salt, and a cellulosic viscosity modifier, wherein the low-strength buffer has a concentration of equal or less than 50 mM, and wherein the low-dose atropine is present at a concentration of equal or less than 0.05 wt %, and wherein the ophthalmic atropine composition is substantially free of a preservative.

For example, the low-dose atropine in such compositions is present at a concentration of equal or less than 0.01 wt %, or is present in the ophthalmic atropine composition in an amount of between 0.01% and 0.02 wt %, or is present in the ophthalmic atropine composition in an amount of between 0.001 wt % and 0.01 wt %. Most typically, the atropine or a pharmaceutically acceptable salt thereof is atropine sulfate, and/or the low-strength buffer comprises a first and a second buffer component (e.g., monobasic and dibasic sodium phosphate). Most typically, the ophthalmic atropine composition has a pH of between 5.0 and 6.0, or a pH of between 5.5 (+/−0.2) and 6.0 (+/−0.2). Contemplated compositions will typically also include a chelator (e.g., a bicarboxylic acid, a tricarboxylic acid, an aminopolycarboxylic acid) that is preferably present in an amount of 0.01 wt % (+/−20% abs.). It is further contemplated that the pharmaceutically acceptable salt is present in the ophthalmic atropine composition in an amount of between 0.2 wt % and 0.8 wt %, or in an amount of 0.5 wt % (+/−0.2 wt %).

Preferred cellulosic viscosity modifiers include a hydroxyethyl cellulose, a hydroxypropyl cellulose, or a hydroxypropyl methylcellulose, typically present in an amount of 0.5 wt % (+/−0.1 wt %) of the ophthalmic atropine composition. In preferred embodiments, the ophthalmic atropine composition is formulated such that after storage over at least two months at 25° C. and 60% relative humidity equal or less than 0.35% tropic acid is formed from degradation of the atropine.

For example, in contemplated compositions the atropine or a pharmaceutically acceptable salt thereof is present in the ophthalmic atropine composition in an amount of between 0.001 wt % and 0.01 wt %, wherein the low-strength buffer comprises monobasic and dibasic sodium phosphate, and wherein the ophthalmic atropine composition has a pH of between 5.5 (+/−0.2) and 6.0 (+/−0.2). In another example, the atropine or a pharmaceutically acceptable salt thereof is present in the ophthalmic atropine composition in contemplated compositions is present in an amount of between 0.001 wt % and 0.01 wt %, wherein the ophthalmic atropine composition further comprises a chelator in an amount of 0.01 wt % (+/−20% abs.) of the ophthalmic atropine composition, and wherein the ophthalmic atropine composition has a pH of between 5.5 (+/−0.2) and 6.0 (+/−0.2). Alternatively, the low-strength buffer in contemplated compositions comprises monobasic and dibasic sodium phosphate, wherein the composition further comprises a chelator in an amount of 0.01 wt % (+/−20% abs.) of the ophthalmic atropine composition, wherein the ophthalmic atropine composition has a pH of between 5.5 (+/−0.2) and 6.0 (+/−0.2), wherein the salt is present in the ophthalmic atropine composition in an amount of 0.5 wt % (+/−0.2 wt %), and wherein the cellulosic viscosity modifier is present in an amount of 0.5 wt % (+/−0.1 wt %) of the ophthalmic atropine composition.

In still another aspect of the inventive subject matter, the inventors also contemplate a method of increasing storage stability of atropine in a liquid low-dose ophthalmic formulation. Typical low-doses are between 0.01 wt % and 0.02 wt %, or between 0.001 wt % and 0.01 wt %, or equal or less than 0.01 wt % of the ophthalmic formulation. Preferred methods will include a step of formulating an aqueous solution with a low-strength buffer system that includes a first and second buffer component, wherein the low-strength buffer system has a concentration of equal or less than 75 mM buffer, and a further step of including into the aqueous solution a pharmaceutically acceptable salt, a viscosity modifier, and a chelator. In still another step, atropine or a pharmaceutically acceptable salt thereof is included into the formulation at a low dose (e.g., equal or less than 0.05 wt % of the ophthalmic formulation), and the pH of the ophthalmic formulation is adjusted to a pH between 5 and 6. Preferably, the ophthalmic formulation is formulated such that after storage over at least two months at 25° C. and 60% relative humidity equal or less than 0.35% tropic acid is formed from degradation of the atropine.

For example, the first and second buffer components are monobasic and dibasic sodium phosphate, respectively, and the low-strength buffer system has a concentration of equal or less than 50 mM buffer. Additionally, it is contemplated that the pharmaceutically acceptable salt is sodium chloride, typically present in the ophthalmic atropine composition in an amount of 0.5 wt % (+/−0.2 wt %) of the ophthalmic formulation. Moreover, it is preferred that the chelator is a bicarboxylic acid, a tricarboxylic acid, or an aminopolycarboxylic acid (e.g., EDTA), preferably in an amount of 0.01 wt % (+/−20% abs.) of the ophthalmic formulation.

In other embodiments, the viscosity modifier is a cellulosic viscosity modifier, such as a hydroxyethyl cellulose, a hydroxypropyl cellulose, or a hydroxypropyl methylcellulose. Most typically the cellulosic viscosity modifier is present in an amount of 0.5 wt % (+/−0.1 wt %) of the ophthalmic formulation. In still further embodiments, the cellulosic viscosity modifier is prepared as a separate solution, and combined with the aqueous solution containing the buffer system, the pharmaceutically acceptable salt, the viscosity modifier, the chelator, and the atropine or the pharmaceutically acceptable salt thereof. Where desired, the aqueous solution is formulated using deoxygenated water. Most typically, the pH of the formulation is between 5.5 (+/−0.2) and 6.0 (+/−0.2), and the atropine or a pharmaceutically acceptable salt thereof is atropine sulfate. Preferably, contemplated methods also include a step of sterilizing the ophthalmic formulation, and especially sterile filtration. As desired, the ophthalmic formulation is then filled into a single-use or multi-dose container.

Additionally, the inventors also contemplate a method of preparing a storage stable liquid low-dose atropine ophthalmic formulation that includes the steps of formulating in a first container a low-strength buffer low-dose atropine solution, and subjecting the low-strength buffer low-dose atropine solution to sterile filtration to obtain a sterile low-strength buffer low-dose atropine solution, wherein the low-strength buffer has a first and a second buffer component that form a low-strength buffer system having a concentration of equal or less than 75 mM in the ophthalmic formulation, wherein the atropine is present in an amount of equal or less than 0.05 wt % of the ophthalmic formulation, and wherein the low-strength buffer low-dose atropine solution further comprises a tonicity agent and a chelator. In another step, a polymer solution is formulated in a second container, and the polymer solution is sterilized in a process other than sterile filtration (e.g., autoclaving) to so obtain a sterile polymer solution. Most typically, the polymer solution comprises a polymer to modify viscosity of the low-strength buffer low-dose atropine solution upon combination. In yet another step, the sterile low-strength buffer low-dose atropine solution and the sterile polymer solution are combined to obtain a sterile liquid low-dose ophthalmic formulation.

Typically, the first and second buffer components are monobasic and dibasic sodium phosphate, respectively, and/or the low-strength buffer system has a concentration of equal or less than 50 mM buffer in the ophthalmic formulation. The atropine is typically present in an amount of between 0.01 wt % and 0.02 wt %, or between 0.001 wt % and 0.01 wt %, or equal or less than 0.01 wt % of the ophthalmic formulation. Most preferably, the tonicity agent is a pharmaceutically acceptable salt, typically sodium chloride in an amount of 0.5 wt % (+/−0.2 wt %) of the ophthalmic formulation. Moreover, the chelator is typically a bicarboxylic acid, a tricarboxylic acid, or an aminopolycarboxylic acid (e.g., EDTA), preferably in an amount of 0.01 wt % (+/−20% abs.) of the ophthalmic formulation.

It is still further contemplated that the polymer is a cellulosic polymer, and especially a hydroxyethyl cellulose, a hydroxypropyl cellulose, or a hydroxypropyl methylcellulose. Preferably, the cellulosic polymer is present in an amount of 0.5 wt % (+/−0.1 wt %) of the ophthalmic formulation, and/or the pH of the low-strength buffer low-dose atropine solution is adjusted to a pH between 5 and 6, or between 5.5 (+/−0.2) and 6.0 (+/−0.2).

In further embodiments, the step of combining comprises mixing the sterile low-strength buffer low-dose atropine solution and the sterile polymer solution for at least 30 minutes, and optionally further comprises a step of filling the ophthalmic formulation into a multi-dose container. Preferably, the ophthalmic formulation is formulated such that after storage over at least two months at 25° C. and 60% relative humidity equal or less than 0.35% tropic acid is formed from degradation of the atropine.

Consequently, the inventors also contemplate a treatment kit for treatment of myopia that includes a first container that contains a liquid storage-stable low-dose atropine ophthalmic formulation, wherein the first container is configured as a disposable single-use container or a multi-dose container, and a second container enclosing the first container, wherein the liquid storage-stable low-dose atropine ophthalmic formulation comprises an aqueous solution comprising a buffer, a tonicity agent, a viscosity modifier, and atropine or a pharmaceutically acceptable salt thereof, wherein the atropine or the pharmaceutically acceptable salt thereof is present in the ophthalmic atropine composition in an amount of equal or less than 0.05 wt %, wherein the buffer has a concentration of equal or less than 75 mM, and wherein the ophthalmic atropine composition has a pH of between 5.0 and 6.0, and wherein the ophthalmic atropine composition is formulated such that after storage over at least two months at 25° C. and 60% relative humidity equal or less than 0.35% tropic acid is formed from degradation of the atropine.

For example, in some embodiments, the first container is a blow-fill-seal (BSF) container and/or the second container is a laminated metallized pouch. In other embodiments, the atropine or pharmaceutically acceptable salt thereof is present in the ophthalmic atropine composition in an amount of equal or less than 0.01 wt %, or in an amount of between 0.01 wt % and 0.05 wt %, or in an amount of between 0.001 wt % and 0.01 wt %. Most preferably, the buffer has a concentration of equal or less than 75 mM, or equal or less than 50 mM. For example, preferred buffers comprise monobasic and dibasic sodium phosphate, and may further comprise a chelator (e.g., a bicarboxylic acid, a tricarboxylic acid, or an aminopolycarboxylic acid such as EDTA) that is present in the ophthalmic atropine composition in an amount of equal or less than 0.01 wt %.

Most typically, the ophthalmic atropine composition has a pH of 5.0 (+/−0.2), or a pH of 5.5 (+/−0.2), or a pH of 6.0 (+/−0.2), and it is further contemplated that the tonicity agent is a pharmaceutically acceptable salt that is present in the ophthalmic atropine composition in an amount of between 0.2 wt % and 0.8 wt %. Preferred viscosity modifiers are modified celluloses such as a hydroxyethyl cellulose, a hydroxypropyl cellulose, or a hydroxypropyl methylcellulose. Still further, it is preferred that the ophthalmic atropine composition is substantially free of a preservative.

Various objects, features, aspects and advantages of the inventive subject matter will become more apparent from the following detailed description of preferred embodiments.

BRIEF DESCRIPTION OF THE DRAWING

FIG. 1 depicts an exemplary production process for the storage stable and low-dose atropine ophthalmic formulation.

DETAILED DESCRIPTION OF THE INVENTION

The inventive subject matter is directed to stable aqueous ophthalmic compositions of atropine (and pharmaceutically acceptable salts thereof) in a ready-to-use form that are sterile and preferably substantially free of preservatives. The stability of contemplated compositions is characterized by low degradation of atropine to tropic acid at low atropine concentrations, as well as by a physiologically desirable pH. For example, liquid and storage-stable low-dose ophthalmic atropine compositions will typically have stability upon storage over at least two months at 25° C. and 60% relative humidity such that equal or less than 0.35% tropic acid is formed by the degradation of atropine in the formulation. Most preferably, the compositions are also free of preservatives, and particularly benzalkonium chloride that is commonly used as a preservative. Such stability is particularly unexpected where the atropine concentration in the ophthalmic composition is relatively low (e.g., 0.02 wt %) and where the composition has a relatively high pH (e.g., between 5.0 and 6.0) as it was generally known that atropine stability decreases at decreasing concentrations and increasing pH.

While not wishing to be bound by any particular theory or hypothesis, the inventors contemplate that low buffer strength using a two-component buffer system at a pH near to a neutral pH (such as pH 5.0-6.0) reduces hydrolysis of atropine to tropic acid where atropine concentrations are relatively low (e.g., equal or less than 0.05 wt %, or equal or less than 0.02 wt %, or equal or less than 0.01 wt %). Unless indicated otherwise, all percentages are weight percentages (wt %) or expressed as weight by volume (w/v Moreover, it is noted that weight percentages of atropine sulfate provided herein are based on atropine sulfate monohydrate.

More specifically, and as is described in more detail below, the inventors discovered that low-dose ophthalmic atropine compositions can be prepared with atropine in a ready-to-use concentration (e.g., for treatment of myopia) that have a near-physiological pH, and that preferably lack any preservative in the formulation. Surprisingly, the storage stability at two months at 25° C. and 60% RH of the ophthalmic compositions presented herein is remarkably high, with tropic acid formation from atropine hydrolysis in most cases at or below 0.35%, at or below 0.30%, or at or below 0.28%. Similarly, contemplated formulations at accelerated storage conditions over two months at 40° C. and 75% RH also exhibited an equally favorable profile with tropic acid formation in most cases at or below 1.7%, at or below 1.5%, at or below 1.3%, or at or below 1.2%.

Therefore, contemplated atropine formulations of the inventive subject matter can be advantageously provided in a ready-to-use format that avoids the inconvenience associated with diluting concentrated atropine formulations into diluents prior to administration. Thus, the ready-to-use formulations also eliminate microbial contamination risks and/or calculation errors associated with dilution. Most typically, contemplated formulations will be available in a range of concentrations commonly required by medical practitioners for treatment of myopia, and particularly pediatric myopia. Consequently, atropine will typically be present in formulations in an amount of equal or less than 0.05 wt %, or in an amount of equal or less than 0.02 wt %, or in an amount of equal or less than 0.01 wt %. For example, the atropine or a pharmaceutically acceptable salt thereof may be present in the ophthalmic composition in an amount of between 0.01% and 0.05 wt %, between 0.001 wt % and 0.02 wt %, or between 0.001 wt % and 0.01 wt %. As will be readily appreciated, atropine for the preparation of contemplated formulations may be atropine or any suitable pharmaceutically acceptable salt thereof, including mineral salts (e.g., HCl salt) and organic salts (e.g., sulfate). Similarly, where desired, the atropine may also be used in any suitable prodrug form.

For example, in one exemplary embodiment, the concentration of atropine in contemplated atropine formulations is from about 0.001% to about 0.05% (w/w); or from about 0.005% to about 0.045% (w/w), or from about 0.006% to about 0.035% (w/w), or from about 0.007% to about 0.030% (w/w), or from about 0.008% to about 0.025% (w/w), or from about 0.009% to about 0.022% (w/w), or from about 0.01% to about 0.021% (w/w) or from about 0.01% to about 0.02% (w/w).

In another exemplary embodiment, the concentration of atropine in contemplated atropine formulations is from about 0.001% to about 0.05% (w/w); or from about 0.005% to about 0.045% (w/w), or from about 0.006% to about 0.035% (w/w), or from about 0.007% to about 0.030% (w/w), or from about 0.008% to about 0.025% (w/w), or from about 0.009% to about 0.022% (w/w), or from about 0.01% to about 0.021% (w/w) or from about 0.01% to about 0.02% (w/w).

In still an exemplary embodiment, the concentration of atropine in contemplated atropine formulations is about 0.001%, or about 0.002%, or about 0.003%, or about 0.004%, or about 0.005%, or about 0.006%, or about 0.007%, or about 0.008%, or about 0.009%, or about 0.01%, or about 0.011%, or about 0.012%, or about 0.013%, or about 0.014%, or about 0.015%, or about 0.016%, or about 0.017%, or about 0.018%, or about 0.019%, or about 0.02%, or about 0.021%, or about 0.022%, or about 0.023%, or about 0.024%, or about 0.025%, or about 0.026%, or about 0.027%, or about 0.028%, or about 0.029%, or about 0.030%, or about 0.031%, or about 0.032%, or about 0.033%, or about 0.034%, or about 0.035%, or about 0.036%, or about 0.037%, or about 0.038%, or about 0.039%, or about 0.040%, or about 0.041%, or about 0.042%, or about 0.043%, or about 0.044%, or about 0.045%, or about 0.046%, or about 0.047%, or about 0.048%, or about 0.049% or about 0.0499% (w/w).

In yet an exemplary embodiment, the concentration of atropine in contemplated atropine formulations is about 0.001%, or 0.002%, or 0.003%, or 0.004%, or 0.005%, or 0.006%, or 0.007%, or 0.008%, or 0.009%, or 0.01%, or 0.011%, or 0.012%, or 0.013%, or 0.014%, or 0.015%, or 0.016%, or 0.017%, or 0.018%, or 0.019%, or 0.02%, or 0.021%, or 0.022%, or 0.023%, or 0.024%, or 0.025%, or 0.026%, or 0.027%, or 0.028%, or 0.029%, or 0.030%, or 0.031%, or 0.032%, or 0.033%, or 0.034%, or 0.035%, or 0.036%, or 0.037%, or 0.038%, or 0.039%, or 0.040%, or 0.041%, or 0.042%, or 0.043%, or 0.044%, or 0.045%, or 0.046%, or 0.047%, or 0.048%, or 0.049% or 0.0499% (w/w).

In further exemplary embodiments, the concentration of atropine in contemplated atropine formulations is from about 0.005% to about 0.015% (w/w), or from about 0.015% to about 0.025% (w/w), or about 0.01% (w/w), or about 0.02% (w/w), or from 0.005% to 0.015% (w/w), or from 0.015% to 0.025% (w/w), or 0.01% (w/w), or 0.02% (w/w), or from about 0.001% (w/w) to about 0.01% (w/w), or from about 0.005% (w/w) to about 0.02% (w/w), or from about 0.008% (w/w) to about 0.012% (w/w).

Suitable buffers are generally buffers that stabilize the pH of the contemplated liquid formulations in a near-neutral pH range, for example between pH 4.0 and 7.5, or between pH 4.5 and 6.5, and more preferably between pH 5.0 and 6.0. Therefore, and most typically the pH of contemplated formulations will be equal or less than 6.5 and more typically equal or less than 6.0, and most typically less than 5.8, but higher than 4.5, more typically higher than 5.0, and most typically higher than 5.2. For example, suitable atropine compositions may have a pH of 5.0 (+/−0.2), or a pH of 5.5 (+/−0.2), or a pH of 6.0 (+/−0.2).

In further aspects of the inventive subject matter, the inventors discovered that the buffer system and/or buffer may have an unexpected influence on atropine stability as is discussed in more detail below. Most notably, once the buffer concentration was adjusted to 75 mM or less at a pH of between 5.0-6.0, the stability of the atropine dramatically increased at normal and accelerated storage conditions as determined by HPLC quantification of tropic acid that is a byproduct of atropine hydrolysis. While not limiting to the inventive subject matter, the buffer strength is typically relatively low, for example, equal or less than 100 mM, equal or less than 75 mM, equal or less than 60 mM, equal or less than 50 mM, or between 5 mM and 50 mM (e.g., 10 mM, 20 mM, 30 mM, 40 mM).

Therefore, in exemplary embodiments, the buffering system is in the pharmaceutical composition in a concentration of from about 10 mM to about 75 mM, or from about 10 mM to about 60 mM, or from about 0.1 mM to about 60 mM, or from about 0.1 mM to about 55 mM, or from about 0.1 mM to about 50 mM, or from about 5 mM to about 60 mM, or from about 0.1 mM to about 10 mM, or from about 1 mM to about 10 mM, or from about 9 mM to about 20 mM, or from about 15 mM to about 25 mM, or from about 19 mM to about 29 mM, or from about 24 mM to about 34 mM, or from about 29 mM to about 39 mM, or from about 34 mM to about 44 mM, or from about 39 mM to about 49 mM, or from about 44 mM to about 54 mM, or from about 19 mM to about 54 mM, or from about 25 mM to about 54 mM.

Of course, it should be appreciated that there are many types of buffer systems and buffers known in the art, and all of those are deemed suitable for use herein, including buffer systems comprising an acid and a salt of the acid, a first and a second salt (e.g., monobasic and dibasic salt), and ampho-teric buffer molecules. For example, suitable buffer systems with an acid and a salt of the acid include citric acid/sodium citrate buffers, ethanoic acid/sodium ethanoate buffers, boric acid/sodium borate, while suitable buffers having a first and a second salt include monobasic sodium phosphate/dibasic sodium phosphate, or monobasic sodium phosphate/sodium citrate, etc. Similarly, suitable amphoteric buffer molecules include HEPES, MOPS, PIPES, MES, etc.

Moreover, in further contemplated aspects, the formulation will also include one or more chelating agents, and particularly metal ion chelators. For example, suitable chelators include various bicarboxylic acids, tricarboxylic acids, and aminopolycarboxylic acids such as ethylenediaminetet-raacetic acid (EDTA), ethylene glycol-bis(β-aminoethyl ether)-N,N,N',N'-tetraacetic acid (EGTA), and penta(car-boxymethyl)diethylenetriamine (DTPA), and salts and hydrates thereof. While not limiting to the inventive subject matter, it is contemplated that the metal ion chelators will slow down both the baseline and metal ion-stimulated hydrolysis of atropine. Remarkably, the inventors unexpect-edly observed that the desirable effect of the chelators was observable at relatively low concentrations of the chelators. For example, reduction of the baseline and metal ion-stimulated hydrolysis of atropine was observed at chelator concentrations of between 10 µg/ml and 50 µg/ml, between 50 µg/ml and 250 µg/ml, and between 100 µg/ml and 500 µg/ml. Viewed form a different perspective, chelator con-centrations of equal or less than 0.03 wt %, or equal or less than 0.02 wt %, or equal or less than 0.01 wt % are especially advantageous. Interestingly, the chelators, and especially the aminopolycarboxylic acids retained stabilizing effect at low concentrations despite the relatively low pH favoring pro-tonated forms of the chelators.

Consequently, suitable chelating agents include mono-meric polyacids such as EDTA, cyclohexanediamine tet-raacetic acid (CDTA), hydroxyethylethylenediamine tri-acetic acid (HEDTA), diethylenetriamine pentaacetic acid (DTPA), dimercaptopropane sulfonic acid (DMPS), dimercaptosuccmic acid (DMSA), aminotrimethylene phos-phonic acid (ATPA), citric acid, ophthalmologically accept-able salts thereof, and combinations of any of the foregoing. Further suitable chelating agents include pyrophosphates, tripolyphosphates, and, hexametaphosphates, chelating antibiotics such as chloroquine and tetracycline, nitrogen-containing chelating agent containing two or more chelating nitrogen atoms within an imino group or in an aromatic ring (e.g., diimines, 2,2'-bipyridines, etc.), and various polyamines such as cyclam (1,4,7,11-tetraazacyclotetradecane), N—($C_1$-$C_{30}$ alkyl)-substituted cyclams (e.g., hexadecyclam, tetramethylhexadecylcyclam), diethylenetriamine (DETA), spermine, diethylnorspermine (DENSPM), diethylhomo-spermine (DEHOP), and deferoxamine (N-'-[5-[[4-[[5-(acetylhydroxyamino)pentyl]amino]-1,4-dioxobutyl]hydroxy-amino]pentyl]-N'-(5-aminopentyl)-N-hydroxybutanediamide; also known as desferrioxamine B and DFO).

With respect to suitable salts it is contemplated that the salt is a pharmaceutically acceptable salt that can be used to increase tonicity. Therefore, pharmaceutically acceptable salts are contemplated, and especially NaCl, at a concentration of at least 0.2 wt %, or at least 0.4 wt %, or at least 0.5 wt %, or at least 0.7 wt %. For example, suitable salt concentrations are between 0.2 wt % and 1.1 wt %, 0.4 wt % and 0.9 wt %, or 0.3 wt % and 0.7 wt %. Depending on the particular salt concentration, additional tonicity agents may be added and suitable tonicity agents include glycerol, thioglycerol, mannitol, lactose, and dextrose. The amount of tonicity adjusting agent used can be adjusted to obtain osmolality of the formulations in the range of 260 to 340 mOsm/kg. An osmometer can be used to check and adjust the amount of tonicity adjusting agent to be added to obtain the desired osmolality.

As contemplated formulations are used as an ophthalmic formulation, it is generally preferred that the formulation also includes a viscosity modifier to adjust the viscosity of the formulation to a dynamic viscosity of between 5 and 50 cP (centipoise), and more preferably between 10 and 40 cP, and most preferably between 10 to 30 cP. While there are numerous viscosity modifiers known in the art such as various polymers, glycerol, and polysaccharidic polymers (all of which are contemplated herein), especially preferred viscosity modifiers include cellulosic viscosity modifiers. For example, particularly preferred cellulosic viscosity modifiers include modified and unmodified hydroxyethyl cellulose, hydroxypropyl cellulose, and hydroxypropyl methylcellulose.

As will be readily appreciated, the exact quantity of the viscosity modifier may vary depending on the type of modifier used and desired final viscosity. For example, where the viscosity modifier is a cellulosic modifier and the final viscosity should be between 1 and 30 cP, suitable quantities of the modifier will typically be in the range of 0.5 wt % (+/−0.1 wt %) of the ophthalmic atropine composition. The person of ordinary skill will be readily able to adjust the viscosity to a desired measure using viscometers (e.g., rotational, vibration, etc.) well known in the art.

In exemplary embodiments, suitable concentrations of the viscosity modifier in contemplated ophthalmic formulations may be any value less than 5% (w/w). For example, suitable concentrations of the viscosity modifier include 0.01% to 4.99% (w/w); or 0.05% to 4.50% (w/w), 0.10% to 3.50% (w/w), 0.15% to 3.00% (w/w), 0.20% to 2.50% (w/w), 0.21% to 2.20% (w/w), 0.22% to 2.10% (w/w), 0.23% to 2.00% (w/w), 0.24% to 1.90% (w/w); 0.25% to 1.80% (w/w), 0.26% to 1.70% (w/w), 0.27% to 1.60% (w/w), 0.28% to 1.50% (w/w), 0.29% to 1.40% (w/w), 0.30% to 1.30% (w/w), 0.31% to 1.2% (w/w), 0.32% to 1.10% (w/w), 0.33% to 1.00% (w/w); 0.34% to 0.90% (w/w); 0.35% to 0.80% (w/w), 0.36% to 0.75% (w/w), 0.37% to 0.70% (w/w), 0.38% to 0.69% (w/w), 0.39% to 0.68% (w/w), 0.40% to 0.67% (w/w), 0.41% to 0.66% (w/w), 0.42% to 0.65% (w/w), 0.43% to 0.64% (w/w), 0.44% to 0.63% (w/w), 0.45% to 0.62% (w/w), 0.45% to 0.61% (w/w), 0.45% to 0.60% (w/w), 0.45% to 0.59% (w/w), 0.45% to 0.58% (w/w), 0.45% to 0.57% (w/w), 0.45% to 0.56% (w/w), 0.45% to 0.55% (w/w), 0.46% to 0.54% (w/w), 0.47% to 0.53% (w/w), 0.48% to 0.52% (w/w) or 0.49% to 0.51% (w/w).

Therefore, appropriate concentrations of the viscosity modifier in contemplated ophthalmic formulations include 0.01%, 0.02%, 0.03%, 0.04%, 0.05%, 0.06%, 0.07%, 0.08%, 0.09%, 0.10%, 0.11%, 0.12%, 0.13%, 0.14%, 0.15%, 0.16%, 0.17%, 0.18%, 0.19%, 0.20%, 0.21%, 0.22%, 0.23%, 0.24%, 0.25%, 0.26%, 0.27%, 0.28%, 0.29%, 0.30%, 0.31%, 0.32%, 0.33%, 0.34%, 0.35%, 0.36%, 0.37%, 0.38%, 0.39%, 0.40%, 0.41%, 0.42%, 0.43%, 0.44%, 0.45%, 0.46%, 0.47%, 0.48%, 0.49%, 0.50%, 0.51%, 0.52%, 0.53%, 0.54%, 0.55%, 0.56%, 0.57%, 0.58%, 0.59%, 0.60%, 0.61%, 0.62%, 0.63%, 0.64%, 0.65%, 0.66%, 0.67%, 0.68%, 0.69%, 0.70%, 0.71%, 0.72%, 0.73%, 0.74%, 0.75%, 0.76%, 0.77%, 0.78%, 0.79%, 0.80%, 0.81%, 0.82%, 0.83%, 0.84%, 0.85%, 0.86%, 0.87%, 0.88%, 0.89%, 0.90%, 0.91%, 0.92%, 0.93%, 0.94%, 0.95%, 0.96%, 0.97%, 0.98%, 0.99%, 1.00%, 1.10%, 1.20%, 1.30%, 1.40%, 1.50%, 1.60%, 1.70%, 1.80%, 1.90%, 2.00%, 2.10%, 2.20%, 2.30%, 2.40%, 2.50%, 2.60%, 2.70%, 2.80%, 2.90%, 3.00%, 3.10%, 3.20%, 3.30%, 3.40%, 3.50%, 3.60%, 3.70%, 3.80%, 3.90%, 4.00%, 4.10%, 4.20%, 4.30%, 4.40%, 4.50%, 4.60%, 4.70%, 4.80%, 4.90% and 4.99% (w/w).

It should further be appreciated that contemplated compositions are substantially free of preservatives (i.e., preservatives not more than 0.01 wt %, and more typically not more than 0.005 wt %). For example, preservatives that are typically not included are benzalkonium chloride, cetrimide or cetrimonium chloride or bromide, benzododecinium bromide, miramine, cetylpyridinium chloride, polidronium chloride or polyquaternium-1, polyquaternium-42 (also known as polixetonium), sepazonium chloride; mercurial derivatives such as the phenylmercury salts (acetate, borate or nitrate), mercuriothiolate sodium (otherwise called thiomersal or thimerosal) and mercurobutol; amidines such as chlorhexidine digluconate or polyhexamethylene biguanide (PHMB); alcohols such as chlorobutanol or phenylethanol or benzyl alcohol or phenol or m-cresol or phenoxyethanol; parabens or esters such as parahydroxybenzoic acid, methylparaben, and propylparaben).

Indeed, the inventors unexpectedly discovered that the formulations without preservatives had the same stability as with preservatives.

With respect to the sterilization of contemplated formulations it should be appreciated that contemplated formulations may be sterilized using all known manners of sterilization, including filtration through 0.22 micron filters, heat sterilization, autoclaving, radiation (e.g., gamma, electron beam, microwave). Advantageously, and as is shown in more detail below, the inventors have also discovered that contemplated formulations can be compounded from two batches in which the viscosity agent is separately sterilized using high-pressure saturated steam at 121° C. (for at least 5, or at least 10, or at least 15 minutes) from the atropine, buffer, and salt solution that was independently filter sterilized.

For example, in one preferred aspect of the inventive subject matter as depicted in the FIGURE, the production of the ophthalmic solution is performed using two distinct production tracks in which the viscosity modifier solution is separately prepared and sterilized from the drug solution. Most notably, such process allowed for rapid and complete dissolution of the atropine, tonicity, buffer components, and chelator, while also enabling a sterilization process that reduces or even entirely eliminates thermal hydrolysis of atropine. Upon preparation of the sterile atropine solution, that solution can then be combined with the viscosity modifier solution that was also sterilized. While conceptually sterilizable using filter sterilization as was the case with the atropine solution, heat sterilization using an autoclave was found to help fully dissolve the viscosity modifier and render the viscous solution readily mixable with the drug solution. Viewed from a different perspective, it should therefore be appreciated that the separate preparation and sterilization process avoided various difficulties that would be otherwise associated with single batch preparation, including increased mixing time of the component to dissolve buffer, tonicity agent, and chelator at increased agitation, increased sterile filtration time due to higher viscosity, etc.

Based on the so achieved stability, the combined solutions contemplated herein can be further filtered through a particle filter (e.g., 40 micron polypropylene filter), and filled in to a polyethylene, polypropylene or low-density polyethylene containers using preformed containers in single-use format or multi-dose format, or using a blow-fill-seal (BFS) process. BFS is a form of advanced aseptic manufacturing wherein the container is formed, filled, and sealed in one continuous, automated system not requiring human intervention. The process begins with the extrusion of plastic granules in the form of a hot hollow pipe of molten plastic called a parison. The next step is the blow molding of the container with an open top through which the container is filled, all while the plastic remains hot and in a molten state. Once filled, the container is hermetically sealed and cooled. The blow-fill seal process can take several seconds, and contemplated ready-to-inject compositions advantageously are formulated to withstand the temperature and pressure requirements without substantial degradation of atropine (e.g., less than 5 wt %, less than 3 wt %, less than 2 wt %, less than 1 wt % degradation).

Once the atropine formulations are filled in large volume polymeric, semi-permeable infusion containers (e.g., BFS container, typically 1.0 mL BFS ampoules), the containers can optionally be layered or covered with a secondary packaging system including an aluminum pouch.

The following examples are provided for illustrative purposes only and should not be interpreted as limiting the present invention.

EXAMPLES

The following examples illustrate some of the experiments leading to the formulations according to the inventive subject matter, however, should not be construed to limit the scope of the claims in any way.

Quantitative Analyses:

A combined test method based on Ultra Performance Liquid Chromatography (UPLC) was developed to perform identification, assay and determination of related compounds in a single run. This was accomplished by using a reversed-phase gradient UPLC with the UV detection including on-line acquisition of UV absorption spectra. Octadecylsilyl-functionalized silica with sub-2 µm particles was used as a stationary phase for chromatographic analysis. The mobile phase is prepared by mixing an aqueous buffer solution with an acidic pH and an acetonitrile-water mixture. Quantification of the active ingredient and related compounds is performed by comparing corresponding peak responses from a Sample Solution to the atropine peak response from a Standard solution. Relative response factors are used to correct for chemical structure effects on the responses. Two identification methods are incorporated into this test method. Atropine is identified based on the retention time of the major peak in the Sample Solution chromatogram and on the UV absorption spectrum acquired within this peak.

Exemplary Formulations And Stability Tests:

Ophthalmic ready-to-use low-dose atropine formulations were prepared using a two-step process substantially as shown in FIG. 1.

Step 1—Preparation of the Polymer Solution Phase: To about 60% of WFI the required quantity of HPMC was added slowly and mixed until a clear solution was observed. The solution was then subjected to autoclaving at 121° C. for a period of about 30 min.

Step 2—Preparation of the Drug Solution Phase: To about 30% of WFI the required quantities of disodium edetate, monobasic sodium phosphate, dibasic sodium phosphate and sodium chloride were added sequentially upon complete dissolution of each ingredient. The pH of the solution was measured and adjusted to about 5.5±0.1 using hydrochloric acid/sodium hydroxide. To the above solution atropine sulfate was added and mixed until there was complete dissolution.

The Drug Solution from Step 2 was then mixed with the Polymer Solution in Step 1. The batch volume was made up using WFI to yield the pharmaceutical composition. Tables 1-3 provide exemplary formulations with and without tonicity agent, with EDTA and low EDTA, and at varying buffer strengths.

TABLE 1

| No. | Ingredient | 100 mM Buffer Composition | | 100 mM Buffer Composition (Low EDTA) | |
| --- | --- | --- | --- | --- | --- |
| | | % w/v | % w/v | % w/v | % w/v |
| 1 | Atropine Sulfate | 0.01 | 0.01 | 0.01 | 0.01 |
| 2 | Sodium Dihydrogen Phosphate Anhydrous | 0.059 | 0.06 | 0.059 | 0.06 |
| 3 | Disodium Hydrogen Phosphate Anhydrous | 1.15 | 1.16 | 1.15 | 1.16 |
| 4 | Edetate Sodium | 0.10 | 0.10 | 0.01 | 0.01 |
| 5 | Sodium Chloride | — | — | — | — |
| 6 | Hypromellose 2910 (Benecel ™ E4M Pharm1) | 0.50 | 0.50 | 0.50 | 0.50 |
| 7 | Hydrochloric Acid | Q.S. for pH adjustment | | Q.S. for pH adjustment | |
| 8 | Sodium Hydroxide | Q.S. for pH adjustment | | Q.S. for pH adjustment | |
| 9 | Water for Injection | Q.S. to 100% | | Q.S. to 100% | |

TABLE 2

| No. | Ingredient | 75 mM Buffer Composition with NaCl | | No Buffer Composition With NaCl | |
| --- | --- | --- | --- | --- | --- |
| | | % w/v | % w/v | % w/v | % w/v |
| 1 | Atropine Sulfate | 0.01 | 0.01 | 0.01 | 0.01 |
| 2 | Sodium Dihydrogen Phosphate Anhydrous | 0.044 | 0.04 | — | — |

TABLE 2-continued

|  |  | 75 mM Buffer Composition with NaCl | | No Buffer Composition With NaCl | |
|---|---|---|---|---|---|
| No. | Ingredient | % w/v | % w/v | % w/v | % w/v |
| 3 | Disodium Hydrogen Phosphate Anhydrous | 0.863 | 0.87 | — | — |
| 4 | Edetate Sodium | 0.1 | 0.1 | 0.1 | 0.1 |
| 5 | Sodium Chloride | 0.15 | 0.15 | 0.9 | 0.91 |
| 6 | Hypromellose 2910 (Benecel™ E4M Pharm1) | 0.5 | 0.5 | 0.5 | 0.5 |
| 7 | Hydrochloric Acid | Q.S. for pH adjustment | | Q.S. for pH adjustment | |
| 8 | Sodium Hydroxide | Q.S. for pH adjustment | | Q.S. for pH adjustment | |
| 9 | Water for Injection | Q.S. to 100% | | Q.S. to 100% | |

TABLE 3

|  |  | 50 mM Buffer Composition without NaCl | | 50 mM Buffer Composition with NaCl | | 50 mM Buffer Composition with NaCl, low EDTA | |
|---|---|---|---|---|---|---|---|
| No. | Ingredient | % w/v | % w/v | % w/v | % w/v | % w/v | % w/v |
| 1 | Atropine Sulfate | 0.01 | 0.01 | 0.01 | 0.01 | 0.01 | 0.01 |
| 2 | Sodium Dihydrogen Phosphate Anhydrous | 0.0295 | 0.03 | 0.0295 | 0.03 | 0.0295 | 0.03 |
| 3 | Disodium Hydrogen Phosphate Anhydrous | 0.575 | 0.58 | 0.575 | 0.58 | 0.575 | 0.58 |
| 4 | Edetate Sodium | 0.1 | 0.1 | 0.1 | 0.1 | 0.01 | 0.01 |
| 5 | Sodium Chloride | — | — | 0.25 | 0.25 | 0.25 | 0.25 |
| 6 | Hypromellose 2910 (Benecel™ E4M Pharm1) | 0.5 | 0.5 | 0.5 | 0.5 | 0.5 | 0.5 |
| 7 | Hydrochloric Acid | Q.S. for pH adjustment | | Q.S. for pH adjustment | | Q.S. for pH adjustment | |
| 8 | Sodium Hydroxide | Q.S. for pH adjustment | | Q.S. for pH adjustment | | Q.S. for pH adjustment | |
| 9 | Water for Injection | Q.S. to 100% | | Q.S. to 100% | | Q.S. to 100% | |

Unless otherwise indicated, pharmaceutical compositions of Table 3 (50 mM Buffer Composition with NaCl) were subjected to long term stability studies. Lab scale batches of atropine sulfate ophthalmic solution were manufactured, (approx. 0.4 mL) filled into 1 mL Blow-Fill-Seal (BFS) ampoules, and were further packaged in aluminum pouches. A number of pouched ampoules were subjected to long term stability studies at 25° C.±2° C./60%±5% RH as per the International Committee on Harmonization stability conditions (see URL: ich.org). Pouched ampoules subjected to these long term stability studies were collected after 1 week, 2 weeks, 3 weeks, 1 month, 2 months, and 3 months of stability storage, opened, and tested for levels of atropine sulfate, tropic acid, pH (where applicable) and viscosity (where applicable). Atropine and tropic acid levels were measured using the UPLC method, and the results are shown in Tables 4-8.

TABLE 4

| | | 100 mM buffered compositions | | | | | | |
|---|---|---|---|---|---|---|---|---|
| | | Long term Stability (25° C./60% RH) | | | | | | |
| Sample Information | Test Parameter | Initial | 1 week | 2 weeks | 3 weeks | 1 month | 2 months | 3 months |
| | Assay of Atropine Sulfate | 101.0 | 101.4 | 102.0 | 101.6 | 101.5 | 101.0 | 100.6 |
| | Viscosity | 23.15 | — | — | — | 24.00 | — | — |
| | pH | 5.52 | 5.55 | 5.55 | 5.51 | 5.53 | 5.66 | 5.58 |
| | Tropic acid (RRT 0.88) | ND | 0.1 | 0.13 | 0.19 | 0.22 | 0.42 | 0.71 |

TABLE 4-continued

|  |  | 100 mM buffered compositions | | | | | | |
|---|---|---|---|---|---|---|---|---|
|  |  | Long term Stability (25° C./60% RH) | | | | | | |
| Sample Information | Test Parameter | Initial | 1 week | 2 weeks | 3 weeks | 1 month | 2 months | 3 months |
|  | Assay of Atropine Sulfate | 104.2 | 103.4 | 103.3 | 103.2 | 101.3 | 102.4 | — |
|  | Tropic acid (RRT 0.88) | ND | 0.07 | 0.08 | 0.12 | 0.15 | 0.30 | — |
|  | Assay of Atropine Sulfate | 98.7 | 97.7 | 98 | 98.1 | 98 | — | — |
|  | pH | 5.55 | 5.40 | 5.41 | 5.42 | 5.43 | — | — |
|  | Tropic acid (RRT 0.88) | ND | ND | 0.07 | 0.09 | 0.12 | — | — |
| Low EDTA | Assay of Atropine Sulfate | 98.2 | 97.3 | 97.7 | 97.7 | 97.1 | — | — |
|  | pH | 5.55 | 5.40 | 5.40 | 5.41 | 5.42 | — | — |
|  | Tropic acid (RRT 0.88) | ND | ND | 0.31 | 0.1 | 0.12 | — | — |

TABLE 5

|  |  | 75 mM buffered with NaCl Compositions | | | | | | |
|---|---|---|---|---|---|---|---|---|
|  |  | Long term Stability (25° C./60% RH) | | | | | | |
| Sample Information | Test Parameter | Initial | 1 week | 2 weeks | 3 weeks | 1 month | 2 months | 3 months |
|  | Assay of Atropine Sulfate | 102.4 | 101.9 | 101.7 | 101.5 | 101.3 | 101.0 | — |
|  | pH | 5.28 | — | — | — | — | — | — |
|  | Tropic acid (RRT 0.88) | ND | 0.05 | 0.08 | 0.1 | 0.15 | 0.33 | — |

TABLE 6

|  |  | 50 mM buffered Without NaCl Compositions | | | | | | |
|---|---|---|---|---|---|---|---|---|
|  |  | Long term Stability (25° C./60% RH) | | | | | | |
| Sample Information | Test Parameter | Initial | 1 week | 2 weeks | 3 weeks | 1 month | 2 months | 3 months |
|  | Assay of Atropine Sulfate | 96.8 | 96.9 | 97.2 | 97.8 | 97.9 | 96.9 | 97.6 |
|  | pH | 5.38 | 5.32 | 5.23 | — | — | — | 5.38 |
|  | Tropic acid (RRT 0.88) | ND | 0.1 | 0.1 | 0.1 | 0.12 | 0.23 | 0.36 |
| Low EDTA | Assay of Atropine Sulfate | 96.1 | 95.9 | 95.6 | 95.6 | 95.9 | — | — |
|  | pH | 5.44 | 5.40 | 5.32 | 5.41 | 5.43 | — | — |
|  | Tropic acid (RRT 0.88) | ND | ND | ND | 0.07 | 0.09 | — | — |

TABLE 7

|  |  | 50 mM buffered with NaCl Compositions | | | | | | |
|---|---|---|---|---|---|---|---|---|
|  |  | Long term Stability (25° C./60% RH) | | | | | | |
| Sample Information | Test Parameter | Initial | 1 week | 2 weeks | 3 weeks | 1 month | 2 months | 3 months |
|  | Assay of Atropine Sulfate | 98.6 | 98.3 | 98.4 | 98.1 | 98 | 97.6 | — |
|  | pH | 5.39 | — | — | — | — | 5.36 | — |
|  | Tropic acid (RRT 0.88) | ND | 0.05 | 0.07 | 0.08 | 0.12 | 0.25 | — |
| Low EDTA | Assay of Atropine Sulfate | 98.8 | 98 | 98 | 98 | 97.9 | — | — |
|  | pH | 5.41 | 5.31 | 5.32 | 5.35 | 5.33 | — | — |
|  | Tropic acid (RRT 0.88) | ND | ND | 0.05 | 0.06 | 0.09 | — | — |

TABLE 8

| | | No Buffer Composition | | | | | | |
|---|---|---|---|---|---|---|---|---|
| | | Long term Stability (25° C./60% RH) | | | | | | |
| Sample Information | Test Parameter | Initial | 1 week | 2 weeks | 3 weeks | 1 month | 2 months | 3 months |
| | Assay of Atropine Sulfate | 103.7 | 103.0 | 103.0 | 103.0 | 102.4 | 101.9 | — |
| | pH | — | — | — | — | — | — | — |
| | Tropic acid (RRT 0.88) | ND | 0.04 | 0.07 | 0.09 | 0.12 | 0.28 | — |

As can be readily seen from the above results, atropine solutions with a reduced amount of buffering system concentration (75 mM, and particularly 50 mM and less) had much lower levels of tropic acid (atropine degradation product) after already 1 month. Regression analysis was used to extrapolate the degradation levels at the end of 24 months. Based on extrapolation methods commonly used in the art, the 50 mM and no buffered concentrations have a shelf life of 18-24 months, which is 3-9 months beyond the 15 month extrapolated shelf life for the 100 mM composition.

The above compositions were also subjected to accelerated stability studies. Lab scale batches of atropine sulfate ophthalmic solution were manufactured, (approx 0.4 mL) filled into 1 mL Blow-Fill-Seal (BFS) ampoules, and were further packaged in aluminum pouches. A number of pouched ampoules were subjected to accelerated stability studies at 40° C.±2° C./75%±5% RH as per the International Committee on Harmonization stability conditions. Pouched ampoules subjected to these accelerated stability studies were collected after 1 week, 2 weeks, 3 weeks, 1 month, 2 months, and 3 months of stability storage, opened, and tested for levels of atropine sulfate, tropic acid viscosity (where applicable). Atropine and tropic acid levels were measured using the UPLC method, and the results are shown in Tables 9-13.

TABLE 9

| | | 100 mM buffered compositions | | | | | | |
|---|---|---|---|---|---|---|---|---|
| | | Accelerated Stability (40° C./75% RH) | | | | | | |
| Sample Information | Test Parameter | Initial | 1 week | 2 weeks | 3 weeks | 1 month | 2 months | 3 months |
| | Assay of Atropine Sulfate | 101.0 | 101.6 | 99.3 | 101.1 | 100.0 | 97.5 | 95.2 |
| | Viscosity | 23.15 | — | — | — | 19.96 | — | — |
| | pH | 5.52 | 5.55 | 5.55 | 5.51 | 5.48 | 5.60 | 5.55 |
| | Tropic acid (RRT 0.88) | ND | 0.3 | 0.76 | 0.79 | 0.97 | 1.98 | 3.02 |
| | Assay of Atropine Sulfate | 104.2 | 103.1 | 102.7 | 102.3 | 101.7 | 99.7 | — |
| | Tropic acid (RRT 0.88) | ND | 0.19 | 0.35 | 0.57 | 0.67 | 1.52 | — |
| | Assay of Atropine Sulfate | 98.7 | 97.6 | 97.4 | 97.1 | 95.6 | — | — |
| | pH | 5.55 | 5.41 | 5.42 | 5.41 | 5.43 | — | — |
| | Tropic acid (RRT 0.88) | ND | 0.14 | 0.32 | 0.46 | 0.58 | — | — |
| Low EDTA | Assay of Atropine Sulfate | 98.2 | 97 | 96.9 | 96.7 | 96.3 | — | — |
| | pH | 5.55 | 5.40 | 5.40 | 5.41 | 5.42 | — | — |
| | Tropic acid (RRT 0.88) | ND | 0.16 | 0.31 | 0.45 | 0.58 | — | — |

TABLE 10

| | | 75 mM buffered with NaCl compositions | | | | | | |
|---|---|---|---|---|---|---|---|---|
| | | Accelerated Stability (40° C./75% RH) | | | | | | |
| Sample Information | Test Parameter | Initial | 1 week | 2 weeks | 3 weeks | 1 month | 2 months | 3 months |
| | Assay of Atropine Sulfate | 102.4 | 101.5 | 101.0 | 100.4 | 99.8 | 98.0 | — |
| | pH | 5.28 | — | — | — | — | — | — |
| | Tropic acid (RRT 0.88) | ND | 0.21 | 0.36 | 0.63 | 0.73 | 1.64 | — |

TABLE 11

50 mM buffered Without NaCl compositions

Accelerated Stability (40° C./75% RH)

| Sample Information | Test Parameter | Initial | 1 week | 2 weeks | 3 weeks | 1 month | 2 months | 3 months |
|---|---|---|---|---|---|---|---|---|
| | Assay of Atropine Sulfate | 96.8 | 97 | 97.5 | 97.6 | 96.9 | 108.6 | 95.1 |
| | pH | 5.38 | 5.31 | 5.25 | — | — | — | 5.37 |
| | Tropic acid (RRT 0.88) | ND | 0.2 | 0.3 | 0.4 | 0.55 | 1.16 | 1.67 |
| Low EDTA | Assay of Atropine Sulfate | 96.1 | 95.1 | 95.3 | 94.9 | 95.2 | — | — |
| | pH | 5.44 | 5.37 | 5.41 | 5.36 | 5.37 | — | — |
| | Tropic acid (RRT 0.88) | ND | 0.1 | 0.21 | 0.31 | 0.42 | — | — |

TABLE 12

50 mM buffered with NaCl compositions

Accelerated Stability (40° C./75% RH)

| Sample Information | Test Parameter | Initial | 1 week | 2 weeks | 3 weeks | 1 month | 2 months | 3 months |
|---|---|---|---|---|---|---|---|---|
| | Assay of Atropine Sulfate | 98.6 | 98.1 | 97.7 | 97.2 | 97.2 | 95.6 | — |
| | pH | 5.39 | — | — | — | — | 5.42 | — |
| | Tropic acid (RRT 0.88) | ND | 0.15 | 0.26 | 0.39 | 0.5 | 1.12 | — |
| Low EDTA | Assay of Atropine Sulfate | 98.8 | 97.6 | 97.3 | 97.1 | 97.1 | — | — |
| | pH | 5.41 | 5.33 | 5.35 | 5.32 | 5.34 | — | — |
| | Tropic acid (RRT 0.88) | ND | 0.09 | 0.23 | 0.34 | 0.45 | — | — |

TABLE 13

No Buffer Composition

Accelerated Stability (40° C./75% RH)

| Sample Information | Test Parameter | Initial | 1 week | 2 weeks | 3 weeks | 1 month | 2 months | 3 months |
|---|---|---|---|---|---|---|---|---|
| | Assay of Atropine Sulfate | 103.7 | 102.9 | 102.4 | 102.2 | 101.7 | 99.9 | — |
| | pH | — | — | — | — | — | — | — |
| | Tropic acid (RRT 0.88) | ND | 0.15 | 0.26 | 0.4 | 0.51 | 1.17 | — |

Once more, it can be readily taken from the data that atropine solutions with a reduced amount of buffering system concentration (75 mM, and particularly 50 mM and less) had much lower levels of tropic acid (atropine degradation product) after already 1 month. Regression analysis was utilized to extrapolate the degradation levels at the end of 24 months. Based on extrapolation methods commonly used in the art, the 50 mM and no buffered concentrations will have a shelf life of 18-24 months, which is 3-9 months beyond the 15 month extrapolated shelf life for the 100 mM composition.

Additional Stability Studies using further variations in composition again established that lower buffer strength, especially with a two component buffer system provide increased stability of the ophthalmic low-dose atropine formulations having compositions as shown in Tables 14-15 at both normal and accelerated storage conditions below (results shown in Tables 16-19.

TABLE 14

| No. | Ingredient | Lot: RD-019-020 mg/mL | Lot: RD-019-023 mg/mL | Lot: RD-001-185 mg/mL |
|---|---|---|---|---|
| 1 | Atropine Sulfate Monohydrate | 0.1 | 0.1 | 0.1 |
| 2 | Monobasic Sodium Phosphate Anhydrous | 0.59 | 0.59 | 0.442 |
| 3 | Dibasic Sodium Phosphate Anhydrous | 11.5 | 11.5 | 8.63 |
| 4 | Edetate Disodium Dihydrate | 1.0 | 0.1 | 1.0 |
| 5 | Sodium Chloride | — | — | 1.5 |
| 6 | Hypromellose 2910 (Benecel E4M Pharm) | 5.0 | 5.0 | 5.0 |
| 7 | Hydrochloric Acid | q.s. for pH adjustment | q.s. for pH adjustment | q.s. for pH adjustment |
| 8 | Sodium Hydroxide | q.s. for pH adjustment | q.s. for pH adjustment | q.s. for pH adjustment |
| 9 | Water for Injection | q.s. to 100% | q.s. to 100% | q.s. to 100% |

TABLE 15

| S. No. | Ingredient | Lot: RD-019-026 mg/mL | Lot: RD-019-029 mg/mL | Lot: RD-001-179 mg/mL |
|---|---|---|---|---|
| 1 | Atropine Sulfate Monohydrate | 0.1 | 0.1 | 0.1 |
| 2 | Monobasic Sodium Phosphate Anhydrous | 0.295 | 0.295 | — |
| 3 | Dibasic Sodium Phosphate Anhydrous | 5.75 | 5.75 | — |
| 4 | Edetate Disodium Dihydrate | 1.0 | 0.1 | 1.0 |
| 5 | Sodium Chloride | — | 2.5 | 9.0 |
| 6 | Hypromellose 2910 (Benecel E4M Pharm) | 5.0 | 5.0 | 5.0 |
| 7 | Hydrochloric Acid | q.s. for pH adjustment | q.s. for pH adjustment | q.s. for pH adjustment |
| 8 | Sodium Hydroxide | q.s. for pH adjustment | q.s. for pH adjustment | q.s. for pH adjustment |
| 9 | Water for Injection | q.s. to 100% | q.s. to 100% | q.s. to 100% |

TABLE 16

| | | Various formulations | | | | | | |
|---|---|---|---|---|---|---|---|---|
| | | Accelerated Stability (40° C./75% RH) | | | | | | |
| Lot Number | Test Parameter | | Initial | 1 week | 2 weeks | 3 weeks | 1 month | 2 months | 3 months |
| Lot: RD-019-020 | pH | | 5.55 | 5.41 | 5.42 | 5.41 | 5.43 | 5.37 | 5.32 |
| | Assay of Atropine Sulfate (%) | | 98.7 | 97.6 | 97.4 | 97.1 | 95.6 | 95.8 | 94.4 |
| | Related Compounds (%) | Tropic acid | ND | 0.14 | 0.32 | 0.46 | 0.58 | 1.45 | 2.20 |
| | | Unknown (RRT = 1.21) | ND | 0.19 | 0.24 | 0.24 | 0.25 | 0.26 | 0.2 |
| | | Apoatropine | ND | ND | 0.05 | 0.06 | 0.06 | 0.12 | 0.17 |
| | | Total impurities | ND | 0.3 | 0.6 | 0.8 | 0.9 | 1.8 | 2.6 |
| Lot: RD-019-023 | pH | | 5.55 | 5.40 | 5.40 | 5.41 | 5.42 | 5.36 | 5.32 |
| | Assay of Atropine Sulfate (%) | | 98.2 | 97 | 96.9 | 96.7 | 96.3 | 95.2 | 94.3 |
| | Related Compounds (%) | Tropic acid | ND | 0.16 | 0.31 | 0.45 | 0.58 | 1.41 | 2.14 |
| | | Unknown (RRT = 1.21) | ND | 0.18 | 0.22 | 0.23 | 0.24 | 0.24 | 0.23 |
| | | Apoatropine | ND | ND | 0.04 | 0.06 | 0.06 | 0.13 | 0.16 |
| | | Total Impurities | ND | 0.3 | 0.6 | 0.7 | 0.9 | 1.8 | 2.5 |
| Lot: RD-001-185 | pH | | 5.28 | NT | NT | NT | NT | 5.46 | NT |
| | Assay of Atropine Sulfate (%) | | 102.4 | 101.5 | 101.0 | 100.4 | 99.8 | 98.0 | 96.2 |
| | Related Compounds (%) | Tropic acid | ND | 0.21 | 0.36 | 0.63 | 0.73 | 1.64 | 2.43 |
| | | Unknown (RRT = 1.21) | ND | 0.23 | 0.25 | 0.25 | 0.25 | 0.25 | 0.25 |
| | | Apoatropine | ND | 0.04 | 0.05 | 0.06 | 0.07 | 0.12 | 0.17 |
| | | Total Impurities | ND | 0.5 | 0.7 | 0.9 | 1.1 | 2.0 | 2.9 |

TABLE 17

| | | Various formulations | | | | | | |
|---|---|---|---|---|---|---|---|---|
| | | Long term Stability (25° C./60% RH) | | | | | | |
| Lot Number | Test Parameter | | Initial | 1 week | 2 weeks | 3 weeks | 1 month | 2 months | 3 months |
| Lot: RD-019-020 | pH | | 5.55 | 5.40 | 5.41 | 5.42 | 5.43 | 5.37 | 5.32 |
| | Assay of Atropine Sulfate (%) | | 98.7 | 97.7 | 98 | 98.1 | 98 | 98.1 | 98.6 |
| | Related Compounds (%) | Tropic acid | ND | ND | 0.07 | 0.09 | 0.12 | 0.29 | 0.44 |
| | | Unknown (RRT = 1.21) | ND | ND | 0.1 | 0.11 | 0.14 | 0.21 | 0.2 |
| | | Apoatropine | ND | ND | ND | ND | ND | ND | 0.04 |
| | | Total impurities | ND | ND | 0.2 | 0.2 | 0.3 | 0.5 | 0.7 |

TABLE 17-continued

Various formulations

Long term Stability (25° C./60% RH)

| Lot Number | Test Parameter | | Initial | 1 week | 2 weeks | 3 weeks | 1 month | 2 months | 3 months |
|---|---|---|---|---|---|---|---|---|---|
| Lot: RD-019-023 | pH | | 5.55 | 5.40 | 5.40 | 5.41 | 5.42 | 5.36 | 5.31 |
| | Assay of Atropine Sulfate (%) | | 98.2 | 97.3 | 97.7 | 97.7 | 97.1 | 98.0 | 97.8 |
| | Related Compounds (%) | Tropic acid | ND | ND | 0.31 | 0.1 | 0.12 | 0.28 | 0.43 |
| | | Unknown (RRT = 1.21) | ND | ND | 0.22 | 0.1 | 0.12 | 0.19 | 0.2 |
| | | Apoatropine | ND | ND | ND | ND | ND | ND | 0.03 |
| | | Total Impurities | ND | ND | 0.2 | 0.2 | 0.2 | 0.5 | 0.7 |
| Lot: RD-001-185 | pH | | 5.28 | NT | NT | NT | NT | 5.49 | NT |
| | Assay of Atropine Sulfate (%) | | 102.4 | 101.9 | 101.7 | 101.5 | 101.3 | 101.0 | 100.6 |
| | Related Compounds (%) | Tropic acid | ND | 0.05 | 0.08 | 0.1 | 0.15 | 0.33 | 0.48 |
| | | Unknown (RRT = 1.21) | ND | ND | 0.1 | 0.13 | 0.16 | 0.21 | 0.23 |
| | | Apoatropine | ND | ND | ND | ND | ND | ND | 0.04 |
| | | Total Impurities | ND | 0.1 | 0.2 | 0.2 | 0.3 | 0.5 | 0.7 |

TABLE 18

Various formulations

Accelerated Stability (40° C./75% RH)

| Lot Number | Test Parameter | | Initial | 1 week | 2 weeks | 3 weeks | 1 month | 2 months | 3 months |
|---|---|---|---|---|---|---|---|---|---|
| Lot: RD-019-026 | pH | | 5.44 | 5.37 | 5.41 | 5.36 | 5.37 | 5.35 | 5.37 |
| | Assay of Atropine Sulfate (%) | | 96.1 | 95.1 | 95.3 | 94.9 | 95.2 | 94.3 | 93.8 |
| | Related Compounds (%) | Tropic acid | ND | 0.1 | 0.21 | 0.31 | 0.42 | 1.00 | 1.53 |
| | | Unknown (RRT = 1.21) | ND | 0.15 | 0.2 | 0.21 | 0.23 | 0.25 | 0.24 |
| | | Apoatropine | ND | ND | 0.04 | 0.05 | 0.06 | 0.10 | 0.15 |
| | | Total Impurities | ND | 0.3 | 0.5 | 0.6 | 0.7 | 1.4 | 1.9 |
| Lot: RD-019-029 | pH | | 5.41 | 5.33 | 5.35 | 5.32 | 5.34 | 5.30 | 5.24 |
| | Assay of Atropine Sulfate (%) | | 98.8 | 97.6 | 97.3 | 97.1 | 97.1 | 97.5 | 95.6 |
| | Related Compounds (%) | Tropic acid | ND | 0.09 | 0.23 | 0.34 | 0.45 | 1.08 | 1.68 |
| | | Unknown (RRT = 1.21) | ND | 0.15 | 0.19 | 0.21 | 0.21 | 0.22 | 0.24 |
| | | Apoatropine | ND | ND | 0.05 | 0.05 | 0.06 | 0.10 | 0.15 |
| | | Total Impurities | ND | 0.2 | 0.5 | 0.6 | 0.7 | 1.4 | 2.0 |
| Lot: RD-001-179 | pH | | 5.52 | NT | NT | NT | NT | 5.58 | NT |
| | Assay of Atropine Sulfate (%) | | 103.7 | 102.9 | 102.4 | 102.2 | 101.7 | 99.9 | 99.0 |
| | Related Compounds (%) | Tropic acid | ND | 0.15 | 0.26 | 0.4 | 0.51 | 1.17 | 1.78 |
| | | Unknown (RRT = 1.21) | ND | 0.25 | 0.28 | 0.28 | 0.28 | 0.29 | 0.29 |
| | | Apoatropine | ND | ND | 0 | 0.05 | 0.05 | 0.08 | 0.11 |
| | | Total Impurities | ND | 0.4 | 0.5 | 0.7 | 0.8 | 1.5 | 2.2 |

TABLE 19

Various formulations

Long term Stability (25° C./60% RH)

| Lot Number | Test Parameter | | Initial | 1 week | 2 weeks | 3 weeks | 1 month | 2 months | 3 months |
|---|---|---|---|---|---|---|---|---|---|
| Lot: RD-019-026 | pH | | 5.44 | 5.40 | 5.32 | 5.41 | 5.43 | 5.31 | 5.30 |
| | Assay of Atropine Sulfate (%) | | 96.1 | 95.9 | 95.6 | 95.6 | 95.9 | 96.2 | 96.5 |
| | Related Compounds (%) | Tropic acid | ND | ND | ND | 0.07 | 0.09 | 0.21 | 0.32 |
| | | Unknown (RRT = 1.21) | ND | ND | ND | ND | 0.11 | 0.18 | 0.20 |
| | | Apoatropine | ND | ND | ND | ND | ND | ND | ND |
| | | Total Impurities | ND | ND | ND | 0.1 | 0.2 | 0.4 | 0.5 |

TABLE 19-continued

|  |  |  | Various formulations | | | | | |
|---|---|---|---|---|---|---|---|---|
|  |  |  | Long term Stability (25° C./60% RH) | | | | | |
| Lot Number | Test Parameter | Initial | 1 week | 2 weeks | 3 weeks | 1 month | 2 months | 3 months |
| Lot: RD-019-029 | pH | 5.41 | 5.31 | 5.32 | 5.35 | 5.33 | 5.26 | 5.25 |
|  | Assay of Atropine Sulfate (%) | 98.8 | 98 | 98 | 98 | 97.9 | 98.0 | 98.5 |
|  | Related Compounds (%) Tropic acid | ND | ND | 0.05 | 0.06 | 0.09 | 0.22 | 0.32 |
|  | Unknown (RRT = 1.21) | ND | ND | ND | ND | 0.1 | 0.17 | 0.2 |
|  | Apoatropine | ND | ND | ND | ND | ND | ND | ND |
|  | Total Impurities | ND | ND | 0.1 | 0.1 | 0.2 | 0.4 | 0.5 |
| Lot: RD-001-179 | pH | 5.52 | NT | NT | NT | NT | 5.45 | NT |
|  | Assay of Atropine Sulfate (%) | 103.7 | 103.0 | 103.0 | 103.0 | 102.4 | 101.9 | 102.2 |
|  | Related Compounds (%) Tropic acid | ND | 0.04 | 0.07 | 0.09 | 0.12 | 0.28 | 0.39 |
|  | Unknown (RRT = 1.21) | ND | 0.09 | 0.14 | 0.16 | 0.2 | 0.26 | 0.28 |
|  | Apoatropine | ND | ND | ND | ND | ND | ND | ND |
|  | Total Impurities | ND | 0.1 | 0.2 | 0.3 | 0.3 | 0.5 | 0.7 |

The effect of pH and stability of compositions of Table 20 was tested and exemplary test results for pH 3.5 and pH 6.0 are provided in the Tables 21-22 (pH 3.5) and Tables 23-24 (pH 6.0) below.

TABLE 20

| No. | Ingredient | Qty/mL |
|---|---|---|
| 1 | Atropine Sulfate Monohydrate | 0.1 mg |
| 2 | Sodium Dihydrogen Phosphate Anhydrous | 0.295 mg |
| 3 | Disodium Hydrogen Phosphate Anhydrous | 5.75 mg |
| 4 | Edetate Disodium Dihydrate | 0.1 mg |
| 5 | Hypromellose 2910, Benecel E4M Pharm | 5.0 mg |
| 6 | Hydrochloric Acid | pH adjustment to 3.5 or 6.0 |
| 7 | Sodium Hydroxide | pH adjustment to 3.5 or 6.0 |
| 8 | Water for Injection | q.s. |

TABLE 21

|  | Accelerated Stability (40° C./75% RH) | | | | | |
|---|---|---|---|---|---|---|
| Test Parameter | Initial | 2 weeks | 1 month | 2 months | 3 months | 6 months |
| Appearance | Clear, colorless solution | Clear, colorless solution | Clear, colorless solution | Clear, colorless solution | Clear, colorless solution | Clear, colorless solution |
| pH | 3.56 | 3.52 | 3.54 | 3.56 | 3.47 | 3.70 |
| Assay of Atropine Sulfate (%) | 99.5 | 99.4 | 98.7 | 98.2 | 98.6 | 97.9 |
| Related Compounds (%) Tropic acid | ND | ND | ND | 0.14 | 0.20 | 0.41 |
| Unknown (RRT = 1.21) | ND | ND | ND | 0.07 | 0.07 | 0.11 |
| Apoatropine | ND | ND | ND | 0.06 | 0.08 | 0.13 |
| Unknown (RRT 0.508) | ND | ND | ND | ND | 0.10 | ND |
| Unknown (RRT 0.683) | ND | ND | ND | ND | ND | 0.20 |
| Total Impurities | ND | ND | ND | 0.3 | 0.4 | 0.6 |

TABLE 22

|  | Accelerated Stability (25° C./60% RH) | | | | | |
|---|---|---|---|---|---|---|
| Test Parameter | Initial | 2 weeks | 1 month | 2 months | 3 months | 6 months |
| Appearance | Clear, colorless solution | Clear, colorless solution | Clear, colorless solution | Clear, colorless solution | Clear, colorless solution | Clear, colorless solution |
| pH | 3.56 | 3.52 | 3.53 | 3.58 | 3.46 | 3.70 |
| Assay of Atropine Sulfate (%) | 99.5 | 99.2 | 98.9 | 98.7 | 98.9 | 98.9 |
| Related Compounds (%) Tropic acid | ND | ND | ND | ND | ND | 0.09 |
| Unknown (RRT = 1.21) | ND | ND | ND | ND | ND | ND |

TABLE 22-continued

| | | Accelerated Stability (25° C./60% RH) | | | | |
|---|---|---|---|---|---|---|
| Test Parameter | Initial | 2 weeks | 1 month | 2 months | 3 months | 6 months |
| Apoatropine | ND | ND | ND | ND | ND | ND |
| Unknown (RRT 0.508) | ND | ND | ND | ND | ND | ND |
| Unknown (RRT 0.683) | ND | ND | ND | ND | ND | ND |
| Total Impurities | ND | ND | ND | ND | ND | 0.1 |

TABLE 23

| | | | Accelerated Stability (40° C./75% RH) | | | | |
|---|---|---|---|---|---|---|---|
| Test Parameter | | Initial | 2 weeks | 1 month | 2 months | 3 months | 6 months |
| Appearance | | Clear, colorless solution | Clear, colorless solution | Clear, colorless solution | Clear, colorless solution | Clear, colorless solution | Clear, colorless solution |
| pH | | 5.99 | 5.87 | 5.89 | 5.83 | 5.83 | 6.00 |
| Assay of Atropine Sulfate (%) | | 108.5 | 106.7 | 104.1 | 99.1 | 95.3 | 84.2 |
| Related Compounds (%) | Tropic acid | ND | 0.90 | 1.91 | 4.17 | 6.07 | 11.26 |
| | Unknown (RRT = 1.21) | ND | 0.32 | 0.32 | 0.29 | 0.29 | 0.27 |
| | Apoatropine | ND | 0.06 | 0.09 | 0.18 | 0.25 | 0.42 |
| | Total Impurities | ND | 1.3 | 2.3 | 4.6 | 6.6 | 12.0 |

TABLE 24

| | | | Accelerated Stability (25° C./60% RH) | | | | |
|---|---|---|---|---|---|---|---|
| Test Parameter | | Initial | 2 weeks | 1 month | 2 months | 3 months | 6 months |
| Appearance | | Clear, colorless solution | Clear, colorless solution | Clear, colorless solution | Clear, colorless solution | Clear, colorless solution | Clear, colorless solution |
| pH | | 5.99 | 5.87 | 5.68 | 5.69 | 5.82 | 6.00 |
| Assay of Atropine Sulfate (%) | | 108.5 | 108.5 | 107.1 | 106.0 | 105.5 | 103.1 |
| Related Compounds (%) | Tropic acid | ND | 0.19 | 0.39 | 0.85 | 1.21 | 2.43 |
| | Unknown (RRT = 1.21) | ND | 0.21 | 0.25 | 0.29 | 0.29 | 0.29 |
| | Apoatropine | ND | ND | ND | 0.05 | 0.05 | 0.08 |
| | Total Impurities | ND | 0.4 | 0.6 | 1.2 | 1.6 | 2.8 |

Atropine sulfate ophthalmic solution is intended to be provided as a single or multi-dose product for topical administration to the eye, which can advantageously be provided as a Blow/Fill/Seal (BFS) ampule as the primary container closure system. For example, suitable ampule materials include Lyondellbasell Purell PE 3020 D resin, which was tested as follows:

Compositions as shown in Table 3 (50 mM Buffer Composition with NaCl, low EDTA), filled in BFS ampoules were tested at concentrations of 0.01% (w/v) and 0.02% (w/v) under accelerated (40° C./75% RH) and long-term (25° C./60% RH) storage conditions. The filled BFS ampoules were then packaged into a secondary packaging (here: laminated pouch) for storage as indicated. The results of this study are presented in Tables 25-28.

TABLE 25

| | | Atropine Concentration 0.01 wt % | | | | | |
|---|---|---|---|---|---|---|---|
| | | Accelerated Storage (40° C./75% RH) | | | | | |
| Test Parameter | | Initial | 2 weeks | 1 month | 2 months | 3 months | 6 months |
| Appearance | | Clear, colorless solution | Clear, colorless solution | Clear, colorless solution | Clear, colorless solution | Clear, colorless solution | Clear, colorless solution |
| pH | | 5.49 | 5.49 | 5.39 | 5.42 | 5.63 | 5.47 |
| Viscosity (cPs) | | 19.96 | NA | NA | NA | 20.48 | 19.48 |
| Assay of Atropine Sulfate (%) | | 104.2 | 104.6 | 102.0 | 102.5 | 99.4 | 93.0 |
| Related Compounds (%) | Tropic acid | NR | 0.41 | 0.89 | 1.73 | 2.66 | 4.67 |
| | Apoatropine | NR | NR | 0.04 | 0.09 | 0.14 | 0.23 |
| | Total impurities | NR | 0.41 | 0.93 | 1.82 | 2.80 | 4.90 |

TABLE 26

| | Atropine Concentration 0.01 wt % | | | | | |
|---|---|---|---|---|---|---|
| | Long-Term Storage (25° C./60% RH) | | | | | |
| Test Parameter | Initial | 2 weeks | 1 month | 2 months | 3 months | 6 months |
| Appearance | Clear, colorless solution | Clear, colorless solution | Clear, colorless solution | Clear, colorless solution | Clear, colorless solution | Clear, colorless solution |
| pH | 5.49 | 5.50 | 5.44 | 5.43 | 5.67 | 5.45 |
| Viscosity (cPs) | 19.96 | NA | NA | NA | 20.56 | 19.42 |
| Assay of Atropine Sulfate (%) | 104.2 | 105.8 | 103.7 | 105.9 | 103.3 | 105.2 |
| Related Compounds (%) Tropic acid | NR | 0.11 | 0.20 | 0.35 | 0.53 | 1.06 |
| Related Compounds (%) Apoatropine | NR | NR | NR | NR | NR | 0.05 |
| Related Compounds (%) Total Impurities | NR | 0.11 | 0.20 | 0.35 | 0.53 | 1.11 |

TABLE 27

| | Atropine Concentration 0.02 wt % | | | | | |
|---|---|---|---|---|---|---|
| | Accelerated Storage (40° C./75% RH) | | | | | |
| Test Parameter | Initial | 2 weeks | 1 month | 2 months | 3 months | 6 months |
| Appearance | Clear, colorless solution | Clear, colorless solution | Clear, colorless solution | Clear, colorless solution | Clear, colorless solution | Clear, colorless solution |
| pH | 5.35 | 5.43 | 5.33 | 5.36 | 5.57 | 5.34 |
| Viscosity (cPs) | 20.26 | NA | NA | NA | 21.20 | 19.82 |
| Assay of Atropine Sulfate (%) | 105.5 | 106.0 | 104.0 | 103.1 | 102.6 | 95.6 |
| Related Compounds (%) Tropic acid | NR | 0.31 | 0.70 | 1.26 | 1.99 | 3.73 |
| Related Compounds (%) Apoatropine | NR | NR | 0.13 | 0.09 | 0.13 | 0.24 |
| Related Compounds (%) Total Impurities | NR | 0.31 | 0.83 | 1.35 | 2.12 | 3.97 |

TABLE 28

| | Atropine Concentration 0.02 wt % | | | | | |
|---|---|---|---|---|---|---|
| | Long-Term Storage (25° C./60% RH) | | | | | |
| Test Parameter | Initial | 2 weeks | 1 month | 2 months | 3 months | 6 months |
| Appearance | Clear, colorless solution | Clear, colorless solution | Clear, colorless solution | Clear, colorless solution | Clear, colorless solution | Clear, colorless solution |
| pH | 5.35 | 5.42 | 5.33 | 5.38 | 5.57 | 5.34 |
| Viscosity (cPs) | 20.26 | NA | NA | NA | 21.17 | 20.17 |
| Assay of Atropine Sulfate (%) | 105.5 | 106.2 | 105.4 | 105.8 | 104.9 | 101.8 |
| Related Compounds (%) Tropic acid | NR | 0.06 | 0.14 | 0.24 | 0.38 | 0.76 |
| Related Compounds (%) Apoatropine | NR | NR | NR | NR | NR | NR |
| Related Compounds (%) Total Impurities | NR | 0.06 | 0.14 | 0.24 | 0.34 | 0.76 |

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

It should be apparent, however, to those skilled in the art that many more modifications besides those already described are possible without departing from the inventive concepts herein. The inventive subject matter, therefore, is not to be restricted except in the spirit of the disclosure. One skilled in the art will recognize many methods and materials similar or equivalent to those described herein, which could be used in the practice of the present invention. Indeed, the present invention is in no way limited to the methods and materials described.

Moreover, in interpreting the disclosure all terms should be interpreted in the broadest possible manner consistent with the context. In particular the terms "comprises" and "comprising" should be interpreted as referring to the elements, components, or steps in a non-exclusive manner, indicating that the referenced elements, components, or steps can be present, or utilized, or combined with other elements, components, or steps that are not expressly referenced.

What is claimed is:

1. A treatment kit for treatment of myopia, comprising:
    a first container that contains a liquid storage-stable low-dose atropine ophthalmic formulation, wherein the first container is configured as a disposable single-use container or a multi-dose container; and
    a second container enclosing the first container;
        wherein the liquid storage-stable low-dose atropine ophthalmic formulation comprises an aqueous solution comprising a buffer, a tonicity agent, a viscosity modifier, and atropine or a pharmaceutically acceptable salt thereof;
        wherein the atropine or the pharmaceutically acceptable salt thereof is present in the ophthalmic atropine composition in an amount of equal or less than 0.05 wt %;
        wherein the buffer has a concentration of equal or less than 75 mM, and wherein the ophthalmic atropine composition has a pH of between 5.0 and 6.0; and
        wherein the ophthalmic atropine composition after storage over at least two months at 25° C. and 60% relative humidity contains equal or less than 0.35% tropic acid formed from degradation of the atropine.

2. The kit of claim 1, wherein the first container is a blow-fill-seal (BSF) container or wherein the second container is a laminated metallized pouch.

3. The kit of claim 1, wherein the atropine or a pharmaceutically acceptable salt thereof is present in the ophthalmic atropine composition in an amount of between 0.01 wt % and 0.05 wt %.

4. The kit of claim 1, wherein the buffer comprises monobasic and dibasic sodium phosphate.

5. The kit of claim 1, wherein the buffer has a concentration of equal or less than 75 mM.

6. The kit of claim 1, wherein the buffer has a concentration of equal or less than 50 mM.

7. The kit of claim 1, wherein the treatment of myopia is treatment of pediatric myopia.

8. The kit of claim 1, further comprising a chelator selected from the group consisting of a bicarboxylic acid, a tricarboxylic acid, and an aminopolycarboxylic acid.

9. The kit of claim 8, wherein the chelator is present in the ophthalmic atropine composition in an amount of equal or less than 0.01 wt %.

10. The kit of claim 1, wherein the ophthalmic atropine composition has a pH of 5.5 (+/−0.2).

11. The kit of claim 1, wherein the tonicity agent is a pharmaceutically acceptable salt and wherein the salt is present in the ophthalmic atropine composition in an amount of between 0.2 wt % and 0.8 wt %.

12. The kit of claim 1, wherein the viscosity modifier is a modified cellulose selected from the group consisting of a hydroxyethyl cellulose, a hydroxypropyl cellulose, or a hydroxypropyl methylcellulose.

13. The kit of claim 1, wherein the ophthalmic atropine composition is substantially free of a preservative.

14. A method of treating myopia, comprising:
    administering to an eye a liquid storage-stable low-dose atropine ophthalmic formulation that comprises an aqueous solution comprising a buffer, a tonicity agent, a viscosity modifier, and atropine or a pharmaceutically acceptable salt thereof;
    wherein the atropine or the pharmaceutically acceptable salt thereof is present in the ophthalmic atropine composition in an amount of equal or less than 0.05 wt %;
    wherein the buffer has a concentration of equal or less than 75 mM, and wherein the ophthalmic atropine composition has a pH of between 5.0 and 6.0; and
    wherein the ophthalmic atropine composition after storage over at least two months at 25° C. and 60% relative humidity contains equal or less than 0.35% tropic acid formed from degradation of the atropine.

15. The method of claim 14, wherein the myopia is a pediatric myopia.

16. The method of claim 14, wherein the atropine or a pharmaceutically acceptable salt thereof is present in the ophthalmic atropine composition in an amount of between 0.01 wt % and 0.02 wt %.

17. The method of claim 14, wherein the buffer has a concentration of equal or less than 50 mM.

18. The method of claim 14, wherein the low-dose atropine ophthalmic formulation further comprises a chelator selected from the group consisting of a bicarboxylic acid, a tricarboxylic acid, and an aminopolycarboxylic acid, and wherein the chelator is present in the ophthalmic atropine composition in an amount of equal or less than 0.01 wt %.

19. The method of claim 14, wherein the low-dose atropine ophthalmic formulation has a pH of 5.5 (+/−0.2).

20. The method of claim 14, wherein the low-dose atropine ophthalmic formulation is substantially free of a preservative.

* * * * *